United States Patent
Mars

(10) Patent No.: US 6,634,236 B2
(45) Date of Patent: Oct. 21, 2003

(54) METHOD AND ARTICLE OF MANUFACTURE FOR ESTIMATING MATERIAL FAILURE DUE TO CRACK FORMATION AND GROWTH

(75) Inventor: William Vernon Mars, Findlay, OH (US)

(73) Assignee: Cooper Technology Services, LLC, Findlay, OH (US)

( * ) Notice: Subject to any disclaimer, the term of this patent is extended or adjusted under 35 U.S.C. 154(b) by 138 days.

(21) Appl. No.: 09/945,058

(22) Filed: Aug. 31, 2001

(65) Prior Publication Data

US 2002/0139194 A1 Oct. 3, 2002

Related U.S. Application Data

(60) Provisional application No. 60/229,416, filed on Aug. 31, 2000.

(51) Int. Cl.[7] ............................................. G01N 29/04
(52) U.S. Cl. ............................................ 73/799; 702/42
(58) Field of Search ......................... 73/799, 808, 809, 73/810, 811, 812, 813, 814, 815; 702/42, 43

(56) References Cited

U.S. PATENT DOCUMENTS

| | | | | | |
|---|---|---|---|---|---|
| 4,709,383 | A | * | 11/1987 | Goto et al. | 378/72 |
| 5,929,315 | A | * | 7/1999 | Dunegan | 73/1.82 |
| 6,449,565 | B1 | * | 9/2002 | Budrow et al. | 702/42 |
| 6,460,012 | B1 | * | 10/2002 | Welch et al. | 702/182 |

* cited by examiner

Primary Examiner—Edward Lefkowitz
Assistant Examiner—Corey D. Mack
(74) Attorney, Agent, or Firm—Fay, Sharpe, Fagan, Minnich & McKee, LLP

(57) ABSTRACT

A multiaxial strain cycle (32, 72) is received that is described by a strain tensor that is a function of time. A hyperelastic constitutive model (34, 74) corresponding to the material is received. A fatigue crack growth curve (36, 76) is obtained. A cracking energy density is calculated (50, 90) based on the constitutive model (34, 74) and the multiaxial strain cycle (32, 72). The cracking energy density is a function of material plane (44, 84) and indicates the portion of the total elastic strain energy density that is available to be released on a selected material plane (48, 88). A cracking plane is determined (54, 98) based upon the cracking energy density. A fatigue life is estimated (60, 100) based on the cracking plane and the fatigue crack growth curve (36, 76).

16 Claims, 3 Drawing Sheets

METHOD AND ARTICLE OF MANUFACTURE FOR ESTIMATING MATERIAL FAILURE DUE TO CRACK FORMATION AND GROWTH

CROSS-REFERENCE TO CO-PENDING PROVISIONAL APPLICATION

This application claims priority from provisional application serial No. 60/229,416 entitled "Multiaxial Fatigue Crack Initiation in Rubber", filed on Aug. 31, 2000, the entire contents of which are expressly incorporated by reference herein.

BACKGROUND OF THE INVENTION

The present invention relates to the materials arts. It particularly relates to the analysis and estimation of fatigue life limited by crack formation and crack growth in materials undergoing applied stresses, especially rubber materials, and will be described with particular reference thereto. However, the invention will also find application in the analysis of other types of structural defects, and is furthermore applicable to materials other than rubbers that are undergoing mechanical stresses.

Models for predicting fatigue life in rubber follow two basic approaches. One approach focuses on predicting crack initiation life, given the history of at-a-point quantities such as stress and strain. The other approach, based on ideas from fracture mechanics, focuses on predicting the propagation of a particular crack, given the energy release rate history of the crack.

Several researchers have applied at-a-point quantities for life predictions in tires and other rubber parts. The quantities investigated have included maximum principal strain or stretch, maximum shear strain, octahedral shear strain, and total strain energy density. For incompressible materials, the total strain energy density is the same as the deviatoric strain energy density. These approaches generally assume that a unique relationship exists between the strain energy density and crack initiation life. While many in the rubber industry have used strain energy density as a predictive parameter for fatigue life, the range of validity of this approach under conditions typically experienced by parts in service has not been adequately investigated.

Fatigue life analysis methods based on fracture mechanics typically presuppose the existence of an initial "test" crack and estimate its propagation under the strain history using iterative finite element analysis methods. Fatigue life is estimated by repeating the finite element analysis for a large plurality of test cracks with different sizes and orientations which are representative of the initial flaws believed to be present in the material. This approach is computationally expensive because each potential failure mode (i.e., test crack) requires its own finite element mesh and analysis. Furthermore, the crack propagation approach requires a priori knowledge of the initial location and state of the crack that causes the final failure. Often, this information is not available, and indeed is the very information the designer needs to predict.

The present invention contemplates an improved fatigue life estimation method which overcomes the aforementioned limitations and others.

SUMMARY OF THE INVENTION

According to one aspect of the invention, a method for estimating fatigue life for a material is disclosed. A multiaxial strain cycle is received that is described by a strain tensor that is a function of time. A hyperelastic constitutive model corresponding to the material is received. A fatigue crack growth curve is obtained. A cracking energy density is calculated based on the constitutive model and the multiaxial strain cycle. The cracking energy density is a function of material plane and indicates the portion of the total elastic strain energy density that is available to be released on a selected material plane. A cracking plane is determined based upon the cracking energy density. A fatigue life is estimated based on the cracking plane and the fatigue crack growth curve.

According to another aspect of the invention, a method for identifying a cracking plane in an elastic material under the action of a tensile multiaxial strain history is disclosed. A cracking energy density $W_c$ is calculated for a material plane. The cracking energy density is incrementally defined by, $$dW_c = \bar{\sigma} \cdot d\bar{\epsilon}$$

with $$\bar{\sigma} = \sigma \bar{r} = \bar{r}^T \sigma, \quad d\bar{\epsilon} = d\epsilon \bar{r}$$

where $dW_c$ is the incremental cracking energy density, $\sigma$ is the stress tensor, $\epsilon$ is the strain tensor, and $\bar{r}$ is a unit vector normal to the material plane. Calculating the cracking energy density $W_c$ is repeated for a selected set of material planes. The cracking plane is identified based on the cracking energy density calculations.

According to yet another aspect of the invention, a program storage medium is readable by a computer and embodying one or more instructions executable by the computer to perform a method for estimating a fatigue life in a material that undergoes a strain history. The method includes the steps of defining a plurality of spatial planes that collectively represent the material planes; calculating cracking energy densities corresponding to the plurality of spatial planes wherein the cracking energy density of a spatial plane indicates the energy available to propagate a crack in that spatial plane; and estimating the fatigue life based on the calculated cracking energy densities.

Numerous advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
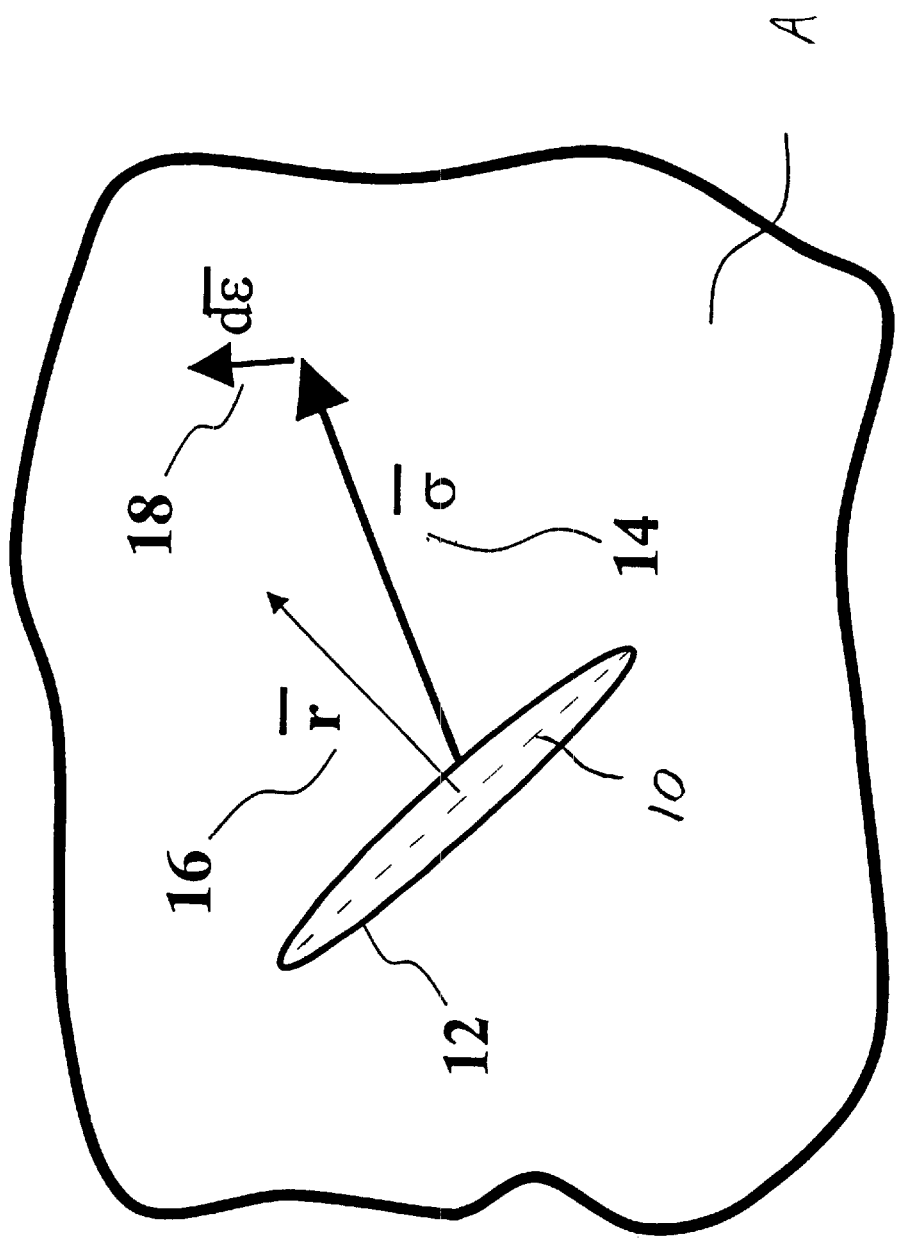
FIG. 1 schematically shows the quantities involved in calculation of the cracking energy density.

With reference to FIG. 1, the cracking energy density (CED) is defined. The CED is the portion of the total elastic strain energy density (SED) that is available to be released on a given plane, e.g. through the nucleation or growth of a crack or other heterogeneous defect. The CED is defined with respect to a spatial material plane 10, which in FIG. 1 includes an exemplary crack 12 embedded in a material A. It will be appreciated by those skilled in the art that real materials (even those which appear macroscopically perfect) contain a certain volume density of heterogeneous structural defects, such as microscopic cracks, microscopic holes, foreign particles, or the like. It is also known that these structural defects typically have a certain size distribution that is characteristic of the material. In the art these intrinsic defects are often characterized by an initial flaw size that is considered an intrinsic property of the material. Thus, the exemplary crack 12 can represent a typical micro-crack of the virgin material having an initial flaw size characteristic of that material.

The cracking energy density (CED) is defined in differential form as:

$$dW_c = \bar{\sigma} \cdot d\bar{\epsilon} \tag{1}$$

where: $dW_c$ is the CED differential; $\bar{\sigma}$ is the traction vector 14 onto the plane 10, i.e.

$$\bar{\sigma} = \sigma \bar{r} = \bar{r}^T \sigma \tag{2}$$

wherein $\sigma$ is the stress tensor and $\bar{r}$ is the plane normal 16; and $d\bar{\epsilon}$ is the strain vector differential 18 associated with the plane 10, i.e.

$$d\bar{\epsilon} = d\epsilon \bar{r} \tag{3}$$

where $d\epsilon$ is the strain differential. By combining equations (1) through (3) and transforming into the principal coordinate system using a transformation $\kappa$, the CED differential or increment can be written as:

$$dW_c = \bar{r}^T \kappa^T \bar{\sigma} d\bar{\epsilon} \kappa \bar{r} \tag{4}$$

In equation (4), the quantities $\sigma$ and $d\epsilon$ have been replaced by $\bar{\sigma}$ and $d\bar{\epsilon}$ to indicate that these quantities are now written in terms of the principal coordinates.

Both the SED and the CED are independent of strain path for elastic materials. Thus, the CED is found by integrating from the unstrained state to the strain state of interest ($\bar{\epsilon}$) along any convenient path. The CED ($W_c$) can be written in integral form as:

$$W_c = \bar{r}^T \kappa^T \left[ \int_0^{\bar{\epsilon}} \bar{\sigma} d\bar{\epsilon} \right] \kappa \bar{r}. \tag{5}$$

The expressions of equations (1) through (5) apply for both rotating and non-rotating tensile strain histories. In equation (5), the expression inside the square brackets contains terms describing the energy density contributed by each stress/strain increment pair in principal coordinates. The expression in brackets will be called the principal strain energy density matrix herein. The strain energy density (SED) is the trace of this matrix. The spatial plane comes into the CED in equation (5) through the plane normal vector $\bar{r}$ in combination with the transformation $\kappa$ outside the square brackets. Thus, it is seen that the CED calculation includes (1) calculating the strain energy density matrix which is independent of the choice of spatial plane, and (2) calculating the CED from the strain energy density matrix, wherein the CED can be viewed as the fraction of the total strain energy density that is available to be released on the plane corresponding to the plane normal $\bar{r}$.

The general equations (1) through (5) which are generally applicable to any material undergoing a tensile strain history are applied in exemplary fashion to an isotropic, linear elastic material. For such a material, the principal stresses are related to the principal strains as:

$$\begin{Bmatrix} \sigma_1 \\ \sigma_2 \\ \sigma_3 \end{Bmatrix} = \frac{2G}{1-2v} \begin{bmatrix} (1-v) & v & v \\ v & (1-v) & v \\ v & v & (1-v) \end{bmatrix} \begin{Bmatrix} \epsilon_1 \\ \epsilon_2 \\ \epsilon_3 \end{Bmatrix}, \tag{6}$$

and the principal strain energy density matrix is written as:

$$\int_0^{\bar{\epsilon}} \bar{\sigma} d\bar{\epsilon} = \tag{7}$$

$$\frac{2G}{1-2v} \begin{bmatrix} (1-v)\epsilon_1^2 + v\epsilon_2\epsilon_1 + v\epsilon_3\epsilon_1 & 0 & 0 \\ 0 & (1-v)\epsilon_2^2 + v\epsilon_3\epsilon_2 + v\epsilon_1\epsilon_2 & 0 \\ 0 & 0 & (1-v)\epsilon_3^2 + v\epsilon_1\epsilon_3 + v\epsilon_2\epsilon_3 \end{bmatrix}.$$

It is emphasized that the equations (1) through (5) are general in nature, and equations (6) and (7) give a particular embodiment thereof.

Figure 2:
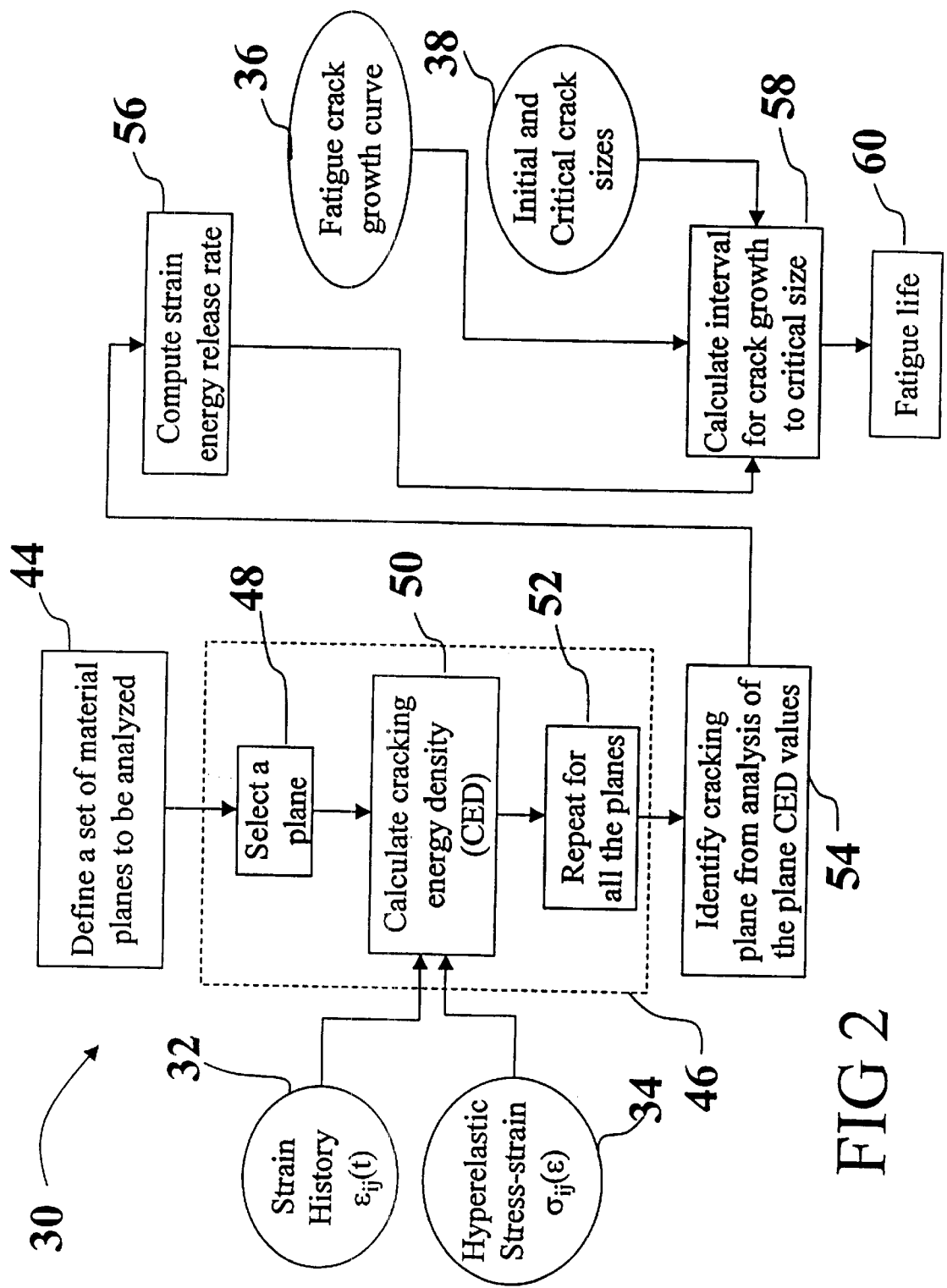
FIG. 2 schematically shows a method for calculating fatigue life that suitably practices an embodiment of the invention.

With reference to FIG. 2, a method 30 for estimating the fatigue life of a material undergoing a particular tensile strain history 32 is described. The method 30 is not restricted with respect to the material type, but is limited to non-rotating strain histories.

In addition to the strain history 32, the method 30 receives as inputs a hyperelastic stress-strain relationship 34, a fatigue crack growth curve 36, and values for the initial crack size and the critical crack size 38. The critical crack size is the size at which the flaw or crack becomes sufficiently large to terminate the useful life of the product comprising the material. The crack growth curve 36 is optionally represented by a complex curve that is numerically implemented using piece-wise integration. However, it is common practice in the art to assume a power-law behavior of the fatigue crack growth curve 36 over the life of the crack or flaw from initial size to critical size. Under this assumption, it is often found that the fatigue crack life is independent of the critical crack size.

The method 30 uses an iterative approach to identify the material plane on which the crack causing the failure will occur. For a non-rotating strain history, this plane is the plane for which the CED is greatest. Thus, a discrete number of material planes to be analyzed are defined in a step 44. These material planes comprise a discrete search space that is searched using an iterative loop 46.

After selecting a material plane in a step 48, the CED is calculated for the selected plane in a step 50. The calculating step 50 evaluates equation (5) for the selected plane, using the strain history 32 and the hyperelastic stress-strain relationship 34 as inputs. It will be appreciated that the method 30 does not involve finite element analyses of the type used in prior art methods of iteratively searching for the cracking plane.

After looping 46 through the material planes, the cracking plane is identified in a step 54 by selecting that plane having the largest CED. This selection is valid for non-rotating strain histories 32.

With the cracking plane identified in the step 54, the time required for a crack to grow from its initial size to the critical size can be calculated by any convenient means. Advantageously, this calculation takes advantage of the CED calculated for the cracking plane in the step 50. In the method 30, a strain energy release rate is calculated in a step 56 from the CED, and the time interval for crack growth from initial to critical sizes is calculated in a step 58. This interval corresponds to the fatigue life 60.

Fatigue crack growth in many materials, including rubber, is driven by the strain energy release rate, even under complex strain histories. The strain energy release rate cannot, in general, be computed from the total strain energy density. The strain energy release rate varies proportionally, for small cracks, with the CED and the crack size. The cracking energy density represents the portion of the total strain energy density that is available to be released on a given material plane. For a non-rotating strain history, crack initiation occurs on the plane that maximizes the cracking energy density, so that the cracking plane can be identified simply by analyzing the CED, e.g. as in step 54.

Figure 3:
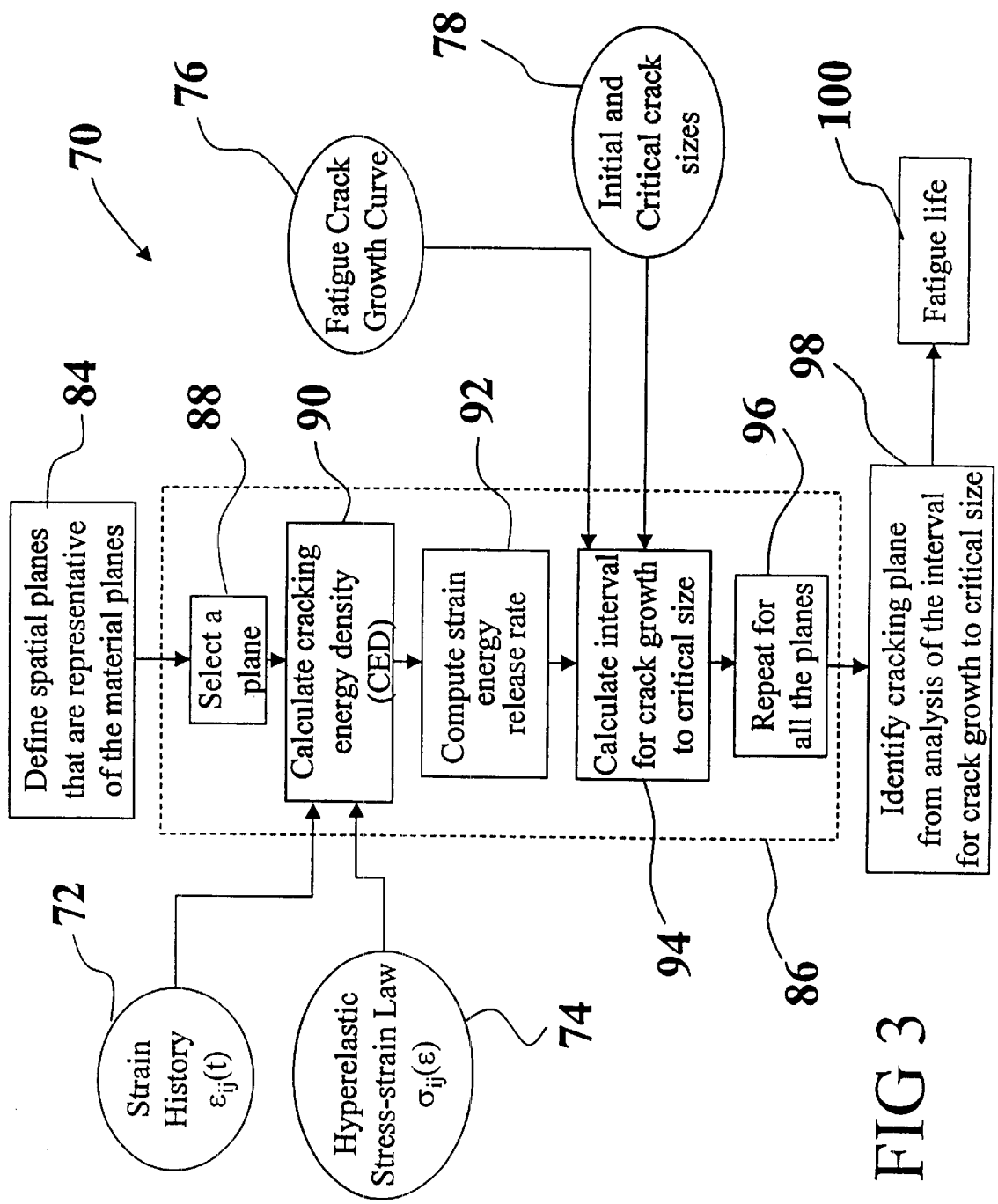
FIG. 3 schematically shows another method for calculating fatigue life that suitably practices another embodiment of the invention.

With reference to FIG. 3, a method 70 is disclosed which is applicable in the general case including rotating strain histories. The method 70 again takes as inputs a multi-axial strain cycle or strain history 72 (which in the method 70 can include rotating strain histories), a material constitutive model or hyperelastic stress-strain relationship 74, a fatigue crack growth curve 76, and values for the initial crack size and the critical crack size 78. Spatial planes representative of the material planes are defined in a step 84, and a loop 86 processes each material plane in turn. A material plane is selected in a step 88, and a CED is calculated for the plane using the strain history 72 and the hyperelastic stress-strain law 74 as inputs.

Because the correspondence between the plane having the maximum CED and the cracking plane is not strictly valid for general (e.g., rotating) strain histories, the method 70 computes the strain energy release rate 92 and the time interval for the crack growth to reach critical size 94 for every material plane, i.e. the computations 92, 94 are included within the loop 86, and the entire loop 86 is repeated for all the material planes in a step 96. With the actual time interval for crack growth to the critical size calculated for each material plane in the loop 86, the fatigue life is obtained in a step 100 by selecting the minimum time interval for a crack to grow to the critical size.

Although the method 70 is more computationally costly versus the method 30, it is still much faster than the prior art methods which repeated finite element analyses for each of the material planes.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method for estimating fatigue life for a material, the method comprising the steps of:
   receiving a multiaxial strain cycle described by a strain tensor that is a function of time;
   receiving a hyperelastic constitutive model corresponding to the material;
   obtaining a fatigue crack growth curve;
   calculating a cracking energy density based on the constitutive model and the multiaxial strain cycle, said cracking energy density being a function of material plane and indicating the portion of the total elastic strain energy density that is available to be released on a selected material plane;
   determining a cracking plane based upon the cracking energy density; and
   estimating fatigue life based on the cracking plane and the fatigue crack growth curve.

2. The method of claim 1, wherein the step of receiving a multiaxial strain cycle further comprises the step of receiving a non-rotating multiaxial strain cycle.

3. The method of claim 2, wherein the the step of determining the cracking plane comprises the step of selecting the cracking plane as the plane that maximizes the cracking energy density.

4. The method of claim 3, wherein the step of estimating fatigue life based on the cracking plane and the fatigue crack growth curve further comprises the steps of:
   computing a strain energy release rate;
   calculating a time interval for a crack having an initial size to grow to a critical crack size; and
   estimating the fatigue life as equaling the calculated time interval.

5. The method of claim 1, wherein the step of receiving a hyperelastic constitutive model corresponding to the material comprises the step of:
   receiving an isotropic, linear constitutive model given by $$\overline{\sigma} = \frac{2G}{1-2v}\begin{bmatrix} (1-v) & v & v \\ v & (1-v) & v \\ v & v & (1-v) \end{bmatrix}$$

where $\overline{\sigma}$ is the constitutive model in principal coordinates, G is the shear modulus of the material, and v is Poisson's ratio of the material.

6. The method of claim 1, wherein the step of determining the cracking plane comprises the steps of:
   selecting a material plane;
   evaluating the cracking energy density for the plane;
   computing a strain energy release rate for the plane;
   calculating a time interval for a crack to grow from an initial size to a critical size in the plane;
   repeating the evaluating step of the cracking energy density, the computing step of a strain energy release rate, and the calculating step of a time interval for a plurality of material planes; and
   defining the fatigue life as the minimum time interval for the plurality of material planes.

7. The method of claim 6, wherein the step of computing a strain energy release rate includes the step computing a strain energy release rate proportional to the cracking energy density and the crack size.

8. The method of claim 1, wherein, conditional upon the multiaxial strain cycle being tensile, the cracking energy density is given by $$\text{cracking energy density} = \bar{r}^T \kappa^T \left[ \int_0^{\bar{\varepsilon}} \bar{\sigma} \, d\bar{\varepsilon} \right] \kappa \bar{r}$$

where $\bar{r}$ is a selected unit vector, $\kappa$ is a coordinate transformation matrix that converts to the principal coordinate system, $\bar{\sigma}$ is the stress tensor in principal coordinates, and $d\bar{\varepsilon}$ is the strain differential in principal coordinates.

9. A method for identifying a cracking plane in an elastic material under the action of a tensile multiaxial strain history, the method comprising the steps of:

calculating a cracking energy density $W_c$ for a material plane, said cracking energy density being incrementally defined by, $$dW_c = \bar{\sigma} \cdot d\bar{\varepsilon}$$

with $$\bar{\sigma} = \sigma \bar{r} = \bar{r}^T \sigma, \quad d\bar{\varepsilon} = d\varepsilon \bar{r}$$

where $dW_c$ is the incremental cracking energy density, $\sigma$ is the stress tensor, $d\bar{\varepsilon}$ is the strain differential and $\bar{r}$ is a unit vector normal to the material plane;

repeating the step of calculating the cracking energy density $W_c$ for a selected set of material planes; and identifying the cracking plane based on the cracking energy density calculations.

10. The method as set forth in claim 9, wherein the step of identifying the cracking plane comprises the further step of identifying the cracking plane as the material plane having the highest cracking energy density, said identifying being conditional on the pre-defined strain history being non-rotational.

11. The method as set forth in claim 9, wherein the step of identifying the cracking plane comprises the steps of:

for each material plane:

estimating a strain energy release rate proportional to the cracking energy density, and calculating a time interval for growth from an initial size to a critical size of a crack in the material plane based on the estimated strain energy release rate; and identifying the cracking plane as the material plane having the smallest time interval for crack growth.

12. An article of manufacture comprising a program storage medium readable by a computer and embodying one or more instructions executable by the computer to perform a method for estimating a fatigue life in a material that undergoes a strain history, the method comprising:

defining a plurality of spatial planes that collectively represent the material planes;

calculating cracking energy densities corresponding to the plurality of spatial planes wherein the cracking energy density of a spatial plane indicates the energy available to propagate a crack in that spatial plane; and estimating the fatigue life based on the calculated cracking energy densities.

13. The article of manufacture as set forth in claim 12, wherein the estimating of the fatigue life based on the calculated cracking energy densities comprises:

identifying the strain history as a non-rotating strain history;

identifying a cracking plane as that spatial plane having the highest calculated cracking energy density;

calculating a time interval for a crack in the cracking plane of a pre-selected initial crack size to grow to a pre-selected critical crack size under the influence of the strain history; and estimating the fatigue life as the time interval.

14. The article of manufacture as set forth in claim 12, wherein the estimating of the fatigue life based on the cracking energy density calculations comprises:

for each of the plurality of planes, computing a time interval for a test crack to grow from an initial size to a final size in the plane, said computing being based on the cracking energy density;

identifying a cracking plane as that plane having the shortest time interval; and estimating the fatigue life as the time interval corresponding to the cracking plane.

15. The article of manufacture as set forth in claim 12, wherein the calculating of cracking energy densities corresponding to the plurality of spatial planes wherein the cracking energy density of a spatial plane indicates the energy available to propagate a crack in that spatial plane comprises:

calculating a differential form of the cracking energy density for a selected spatial plane;

integrating the differential form of the cracking energy density for the selected spatial plane over the strain history; and repeating the calculating of a differential form and the integrating of the differential form for each of the plurality of spatial planes.

16. The article of manufacture as set forth in claim 15, wherein the calculating of a differential form of the cracking energy density for a selected spatial plane comprises:

calculating the differential form $dW_c$ according to $$dW_c = \bar{\sigma} \cdot d\bar{\varepsilon}$$

with $$\bar{\sigma} = \sigma \bar{r} = \bar{r}^T \sigma, \quad d\bar{\varepsilon} = d\varepsilon \bar{r}$$

where $\sigma$ is the stress tensor, $\varepsilon$ is the strain tensor, and $\bar{r}$ is a unit vector that is normal to the selected spatial plane.

* * * * *